(12) United States Patent
Peng et al.

(10) Patent No.: US 9,962,351 B2
(45) Date of Patent: May 8, 2018

(54) SMALL MOLECULE SUBSTANCE FOR IMPROVING SENSITIVITY OF BACTERIA TO ANTIBIOTICS

(71) Applicant: Sun Yat-Sen University, Guangzhou, Guangdong (CN)

(72) Inventors: Xuanxian Peng, Guangdong (CN); Hui Li, Guangdong (CN); Xianliang Zhao, Guangdong (CN)

(73) Assignee: SUN YAT-SEN UNIVERSITY (CN)

( * ) Notice: Subject to any disclaimer, the term of this patent is extended or adjusted under 35 U.S.C. 154(b) by 101 days.

(21) Appl. No.: 14/649,667

(22) PCT Filed: Dec. 4, 2012

(86) PCT No.: PCT/CN2012/085868
§ 371 (c)(1),
(2) Date: Jun. 4, 2015

(87) PCT Pub. No.: WO2014/085989
PCT Pub. Date: Jun. 12, 2014

(65) Prior Publication Data
US 2015/0297547 A1 Oct. 22, 2015

(51) Int. Cl.
| | | |
|---|---|---|
| *A61K 31/198* | (2006.01) | |
| *A61K 31/43* | (2006.01) | |
| *A61K 31/7004* | (2006.01) | |
| *A61K 31/4709* | (2006.01) | |
| *A61K 31/496* | (2006.01) | |
| *A61K 31/546* | (2006.01) | |
| *A61K 31/7036* | (2006.01) | |
| *A61K 31/7048* | (2006.01) | |
| *A61K 31/7056* | (2006.01) | |

(52) U.S. Cl.
CPC ............ *A61K 31/198* (2013.01); *A61K 31/43* (2013.01); *A61K 31/4709* (2013.01); *A61K 31/496* (2013.01); *A61K 31/546* (2013.01); *A61K 31/7004* (2013.01); *A61K 31/7036* (2013.01); *A61K 31/7048* (2013.01); *A61K 31/7056* (2013.01)

(58) Field of Classification Search
CPC .. A61K 39/0011; A61K 39/39; A61K 31/706; A61K 31/7028; A61K 31/7056; A61K 2300/00; C07D 493/04; C07D 493/08; C07H 15/04; C07H 15/14; C07H 15/26; C07H 19/01; C07H 5/10
USPC .......... 424/277.1, 279.1; 536/17.4, 17.6, 53; 549/363
See application file for complete search history.

(56) References Cited

U.S. PATENT DOCUMENTS

2008/0254010 A1* 10/2008 Sasser .................. A61K 31/195
424/93.44

FOREIGN PATENT DOCUMENTS

CN 102920719 A 2/2013

OTHER PUBLICATIONS

The Merck Manual, 1992, pp. 183-189.*
Mazloomi et al, International Immunopharmacology, 2011, 11, 2214-19.*
Tallarida, The Journal of Pharmacology and Experimental Therapeutics, 2001, 298, 865-872.*
Ebrahim Mazloomi et al., "Synergistic effects of glutamine and ciprofloxacin in reduction of Pseudomonas aeruginosa-induced septic shock severity" International Immunopharmacology, vol. 11, Oct. 19, 2011.
Xin-Ming Yu et al., "The Effect of Replacing Antibiotics Feed Additive with Gluconic Acid, Glut amine and their Combination of Production Performance of the Piglets" Xinjiang Agricultural Sciences, vol. 49, No. 1, Jan. 31, 2012.
International Search Report issued in Application No. PCT/CN2012/085868 dated Sep. 12, 2013.

* cited by examiner

Primary Examiner — Ganapathy Krishnan
(74) Attorney, Agent, or Firm — Cooper Legal Group, LLC

(57) ABSTRACT

Disclosed is a new function of a small molecule metabolite glutamine. The small molecule can improve sensitivity of bacteria including antibiotic-resistant bacteria to antibiotics. Also disclosed is an application of glutamine in combination with glucose in improving sensitivity of bacteria to antibiotics.

4 Claims, 8 Drawing Sheets

SMALL MOLECULE SUBSTANCE FOR IMPROVING SENSITIVITY OF BACTERIA TO ANTIBIOTICS

TECHNOLOGICAL FIELD

The present invention belongs to the field of medicine technology. More particularly, the present invention relates to a small molecule substance which is glutamine for enhancing susceptibility of bacteria to antibiotics.

BACKGROUND OF THE INVENTION

Invention and application of antibiotics play a crucial role in protecting the health and life of human. However, overuse of antibiotics causes antibiotic-resistant bacteria, which threats to the human health, domestic animals, aquaculture and environment. According to the statistics of Ministry of Health, approximate eighty thousands of people directly or indirectly died of antibiotics abuse annually in China. And the losses causing by health-harming and generation of antibiotic resistant bacteria are uncountable. The antibiotic resistant bacteria isolated some clinical in China are on the top of the world. Antibiotic resistance rate of quinolones arrives at 60-70% though the class of antibiotics are used in China for only twenty years besides penicillins-resistant *Streptococcus pneumonia*, methicillin-resistant *staphylococcus aureus, enterococcus* and fungal.

In animal husbandry, antibiotics are essential as veterinary medicaments. If veterinary medicaments are not used, the feed number of poultry and livestock required should increase 25% and 89%, respectively. However, wide use and even abuse of veterinary medicaments, especially subclinical dose use for the growth promotion, causes a great death of non-resistant bacteria, and help the antibiotic-resistant bacteria to breed at a prolific rate, which leads to more resistant to antibiotic. In aquaculture, antibiotics are used to control bacterial pathogens. The overuse of antibiotics leads to emerging antibiotic-resistant strains and low quality of aquatic products, which is a seriously threat to aquaculture. Food safety problems with antibiotic residue caused by antibiotic abuse not only reduce export economy, but also increase antibiotic resistant bacteria and make the aquaculture environment worse, which are the direct or indirect threat to ecological environment.

There is a dose-effect relationship between the use of antibiotics and the resistance level of pathogens, i.e. the use of antibiotics within a certain range can change the pathogens antibiotic-resistance level and infection rate of antibiotic resistant bacteria, and then the normal intestinal microflora of human and animal develop resistance to antibiotics, and pollute the environment, water and food by animal feces. So the antibiotic resistant bacteria are increase and the probability to contact with antibiotic resistant bacteria is also increased. Thus, the species of antibiotic resistant bacteria are isolated and identified widely. These antibiotic resistant bacteria cause infectious diseases, which is difficult to be cured since these pathogens are not sensitive to antibiotics. The control of antibiotic resistant bacteria has become a social and scientific issue. In world health day 2011, "Combat with antibiotic resistance: no action today, no medicine tomorrow" was raised by World Health Organization (WHO). Although the development of new antibiotics speeds up with the appearance of antibiotic resistant bacteria, new antibiotic resistant bacteria appear rapidly when the new antibiotics are used. Moreover, the development of a new antibiotic needs a long time. These indicate that strategy on development of new antibiotics may not control the widespread of antibiotic resistant bacteria. These antibiotic resistant bacteria are a great challenge to develop new antibiotics and control the bacterial infectious diseases. Therefore, new methods to inhibit the antibiotic resistant bacteria are very important to control the infections caused by antibiotic resistant pathogens, and to safeguard human health, promote ecological breeding and guarantee food safety. It has been found that plant extracts, traditional Chinese medicine, rinse-free disinfectants are efficient in inhibiting multi antibiotic resistant bacteria in vitro. However, they contain complex components and the specific substances playing the key role are unknown. Recent studies have found that some small molecule metabolites such as glucose and fructose can improve the sensitivity of bacterial persisters gram-negative (*Escherichia coli*) and gram-positive (*Staphylococcus aureus*) to aminoglycosides. The result was specific to this class of antibiotic, and it was further verified in mice. Although bacterial persisters are not the antibiotic resistant bacteria, it is with high tolerance to antibiotics. Besides this report, information regarding to the metabolites or small molecule substances for improving the sensitivity of bacteria to antibiotics is not available so far.

SUMMARY OF THE INVENTION

The aim of the invention is to provide glutamine (Glu/L, CAS 56-85-9), a kind of small molecule metabolite for enhancing susceptibility of bacteria to antibiotics, to inhibit the growth of bacteria including antibiotic resistant bacteria. All small molecule metabolites of ampicillin-resistant bacteria were analyzed with the method of metabolomics basing on gas chromatography-mass spectrometry (GC-MS). It is found the amount of glutamine in ampicillin-resistant bacteria was decrease significantly. And the amounts of glutamine in all of five species of antibiotic resistant bacteria decreased in the further analysis. These results indicated that glutamine may be a small molecule metabolite to improve the susceptibility of antibiotic-resistant bacteria to antibiotics. The survival rates of antibiotic-resistant bacteria decreased significantly when added with glutamine, indicating that glutamine can increase the susceptibility of antibiotic-resistant bacteria to antibiotics. Furthermore, after added with glutamine, the survival rates of antibiotic-resistant bacteria to ampicillin dramatically declined, indicating that the sensitivity of antibiotic-resistant bacteria to ampicillin was improved after added with glutamine. In the control group, susceptibility of non-resistant bacteria to antibiotics was also improved. Similar results were also found in the other three kinds of penicillin antibiotics. Moreover, glutamine was demonstrated to improve the susceptibility of *Escherichia coli* to tetracycline, erythromycin, clindamycin and rifampicin. These results showed that the combined utilization of antibiotics and glutamine, capable of improving the susceptibility of bacteria to antibiotics, can be used to treat the disease caused by antibiotic resistant and non-resistant bacteria. Particularly, it is commonly found that the combined utilization of ampicillin and glutamine can inhibit the viability of antibiotic-resistant bacteria. Furthermore, in the present invention, after added with glucose, the survival rates of ampicillin-resistant bacteria decreases significantly when treated with ampicillin and glucose, indicating that glucose can improve the susceptibility of ampicillin-resistant bacteria to ampicillin. Synergistic effect was found when added with glutamine and glucose together in the further study in which glutamine and glucose are used in combination. In the present invention, the combined utilization of glutamine and ampicillin was proved to effectively remove the bacteria on biofilm which was constructed in vitro. Furthermore, mice model with chronic urinary tract infection was adopted, and the biofilm of antibiotic-resistant bacteria was implanted in urethra, then glutamine and ampicillin were injected for treatment. Results showed that in the group treated with glutamine and ampicillin bacteria was killed effectively. When detecting bacterial content in kidney tissue, it is found the bacterial content significantly declined when treated with glutamine and ampicillin, indicating that combined utilization of these two substances was an effective treatment to the bacterial infection in kidney. These results indicated antibiotic-resistant bacteria in animals can be removed with the combined utilization of glutamine and antibiotic. Meanwhile, the survival rates of ampicillin-resistant bacteria declined significantly when treated with ampicillin after added with glucose to mice. It means that glucose in animal bodies can improve the sensitivity of ampicillin-resistant bacteria to ampicillin. According to the in vivo animal test using glutamine and glucose in combination, it is found that these two kinds of additives had significant synergistic effect.

In conclusion, the sensitivity of antibiotic resistant bacteria and non-resistant bacteria to antibiotics is improved when glutamine is added into antibiotic(s). A new method to the elimination of antibiotic-resistant bacteria is provided.

Accordingly, the invention discloses and protects the use of glutamine to improve the susceptibility of bacteria to antibiotics. The invention can be used to prepare bacteriostatic or bactericidal medicaments and enhance the susceptibility of bacteria or antibiotic-resistant bacteria to antibiotics.

Meanwhile, the invention discloses and protects the method of improving the susceptibility of bacteria to antibiotics, wherein glutamine and antibiotics are used in combination.

The bacteria include but are not limit to *Staphylococcus aureus, Beta hemolytic streptococcus, Escherichia coli, Pseudomonas aeruginosa, Edwardsiella tarda, Vibrio parahaemolyticus* and *Vibrio alginolyticus*. They are common human and farming animal pathogens. *Staphylococcus aureus* and *Beta hemolytic streptococcus* are gram-positive bacterium, *Escherichia coli, Pseudomonas aeruginosa, Edwardsiella tarda, Vibrio parahaemolyticus* and *Vibrio alginolyticus* are gram-negative bacterium. They are antibiotic-sensitive or antibiotic-resistant bacteria. These bacteria are common pathogenic bacteria and the resistant strains of them are common. *Escherichia coli, Pseudomonas aeruginosa* and *Staphylococcus aureus* are model bacteria for antibiotic resistance study.

The antibiotics include but are not limit to penicillins ampicillin, amoxicillin, penicillin G and carbenicillin, cephalosporin carbenicillin (penicillins and cephalosporin consists β-lactams), quinolones balofloxacin and nalidixic acid, aminoglycoside gentamicin and kanamycin, macrolides erythromycin, tetracycline tetracycline, rifamycins rifampicin and lincosamides clindamycin. These have covered the major class of antibiotics in clinical use.

The rate of the glutamine described above to antibiotic is 1:0.0015-300 by weight.

In some embodiments, the concentration of glutamine is 3 mg-30 g/time for administration when it is used to improve the sensitivity of bacteria to antibiotics according to the above described method.

By the disclosure of the present invention, new bacteriostatic or bactericidal agents can be prepared, which contain antibiotic and glutamine. Or, a new agent for improving antibiotics' bacteriostatic or bactericidal effect relating antibiotic-resistant bacteria can be prepared, containing glutamine and antibiotic(s) as main components.

In the embodiments of the present invention, the bacteria include *Staphylococcus aureus, Beta hemolytic streptococcus, Escherichia coli, Pseudomonas aeruginosa, Edwardsiella tarda, Vibrio parahaemolyticus* and *Vibrio alginolyticus*. Especially, *Escherichia coli* are studied in the most of verification tests. However, they are non-limiting examples of bacterial species. This is because for the following reasons: 1) *Escherichia coli, Pseudomonas aeruginosa* and *Staphylococcus aureus* are models of bacteria used for studying of antibiotic resistant mechanisms. 2) They are classified into gram-negative or gram-positive microbes. *Staphylococcus aureus* and *Beta hemolytic streptococcus* are gram-positive microbes, and *Escherichia coli, Pseudomonas aeruginosa, Edwardsiella tarda, Vibrio parahaemolyticus* and *Vibrio alginolyticus* are gram-negative microbes. Gram staining is usually used for classification of human and farming animal pathogens. Thus, the above mentioned bacteria in the invention are good representatives of bacterial pathogens. 3) Bacteria may be classified into antibiotic resistant and non-resistant statuses, meaning antibiotic resistant and non-resistant strain may originate from a bacterium. The control bacteria in the invention are non-resistant, relatively compared, while, they also become susceptibility to antibiotics after added with glutamine. Thus, according to the present invention, more bacterial pathogens can be expected to be applicable according to the bacteria disclosed herein.

In the embodiments of the present invention, antibiotics include ampicillin, amoxicillin, penicillin G, carbenicillin, ceftazidime, balofloxacin, nalidixic acid, gentamicin, kanamycin, erythromycin, tetracycline, rifampicin and clindamycin. However, they are non-limiting examples of antibiotics. This is because antibiotics were classified dependent on chemical structures and antibacterial mechanisms. Similar chemical structures posses the same antibacterial mechanisms although there are hundreds of antibiotics in clinic. Therefore it is reasonable that it is not necessary to validate all antibiotics one by one. Antibiotics used in clinical mainly include penicillins, cephalosporin, quinolones, aminoglycoside, macrolides, tetracyclins, rifamycins and lincosamides. In the embodiments of the present invention, ampicillin is classified to penicillins, ceftazidime is classified to cephalosporin, balofloxacin and nalidixic acid are classified to quinolones, gentamicin and kanamycin are classified to aminoglycoside, erythromycin is classified to macrolides, tetracycline is classified to tetracyclins, rifampicin is classified to rifamycins and clindamycin is classified to lincosamides. Thus, these are good representative of antibiotics. Thereby, according to the concept of the present invention, it can be expected by the person skilled in the art that other antibiotics can be used in present invention.

Synergistic effect of glutamine and glucose is found in improving the sensitivity of bacteria to antibiotics.

Preferably, the ratio of glutamine to glucose is 1:0.0001-10000 by weight.

Preferably, antibiotics is/are selected from the group containing ampicillin, amoxicillin, penicillin G, carbenicillin, ceftazidime, balofloxacin, nalidixic acid, gentamicin, kanamycin, erythromycin, tetracycline, rifampicin and clindamycin.

FIGURES

Preferably, antibiotics is/are selected from the group containing ampicillin, amoxicillin, penicillin G, carbenicillin, ceftazidime, balofloxacin, nalidixic acid, gentamicin, kanamycin, erythromycin, tetracycline, rifampicin and clindamycin.

Figure 4A:
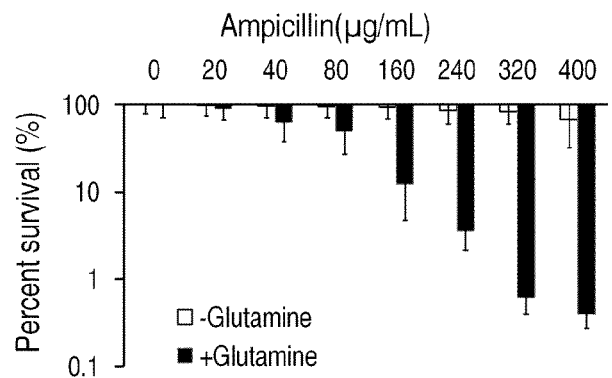
Figure 4B:
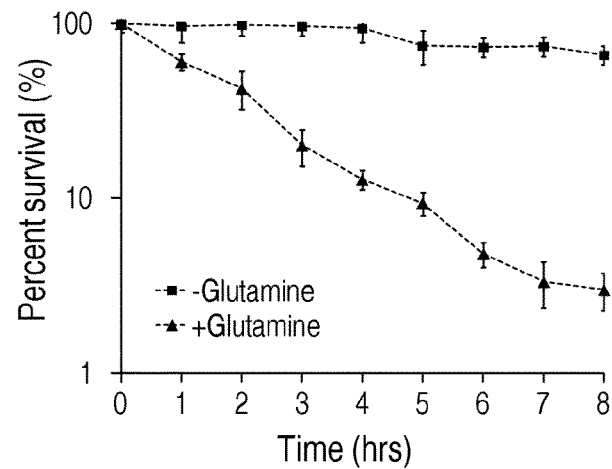
Figure 4C:
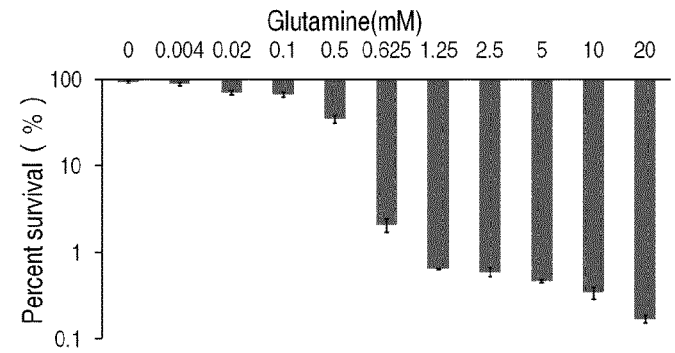

FIG. 4A shows the effect of glutamine on the susceptibility of ampicillin-resistant bacteria (AMP-R) to ampicillin (AMP) in terms of ampicillin concentration; FIG. 4B shows the effect of glutamine on the susceptibility of ampicillin-resistant bacteria (AMP-R) to ampicillin (AMP) in terms of exposure time; and FIG. 4C shows the effect of glutamine on the susceptibility of ampicillin-resistant bacteria (AMP-R) to ampicillin (AMP) in terms of glutamine concentration.

Figure 5:
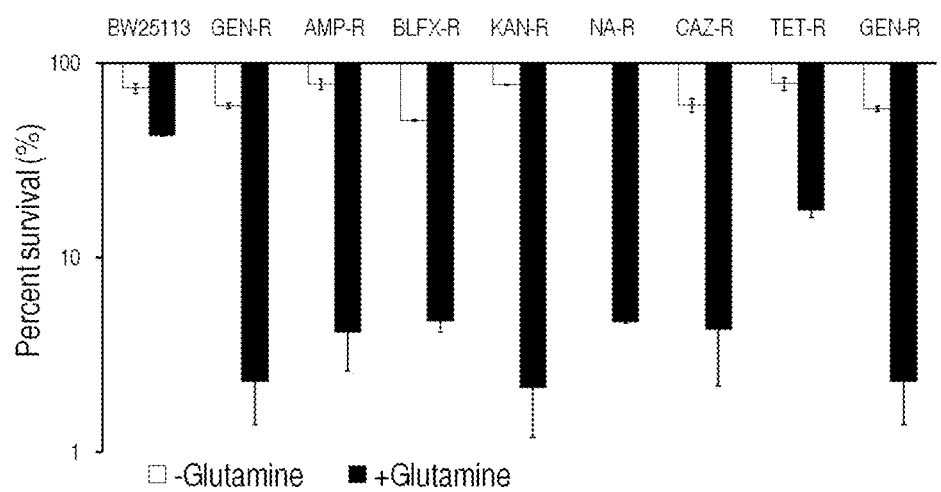

FIG. 5 shows the effect of glutamine on the susceptibility of several species of ampicillin-resistant *Escherichia coli* to ampicillin.

Figure 6A:
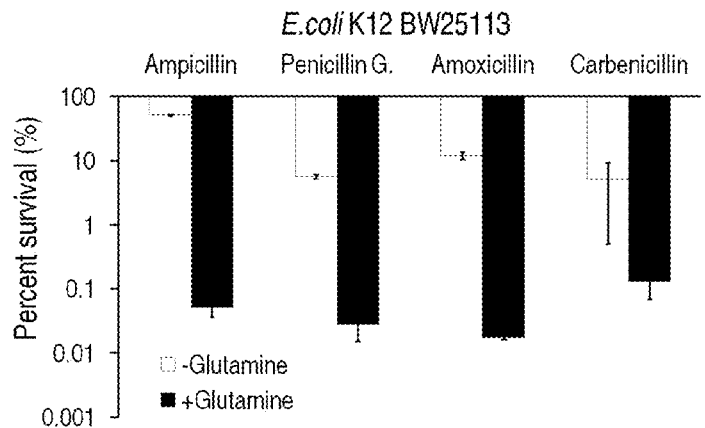
Figure 6B:
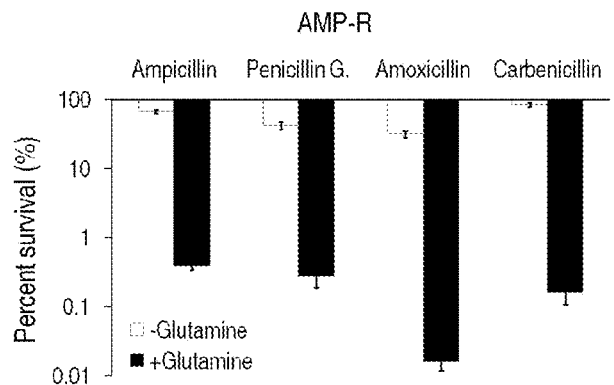
Figure 6C:
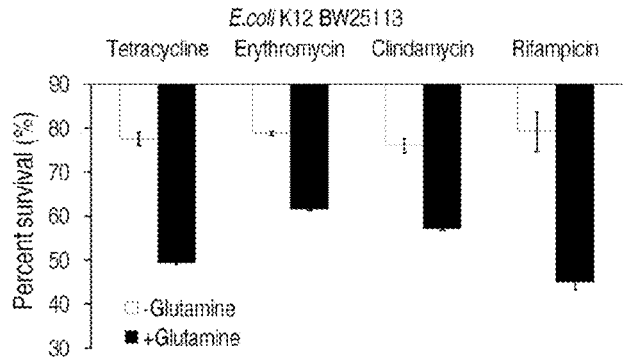

FIGS. 6A and 6B show the effect of glutamine on the susceptibility of *Escherichia coli* and ampicillin-resistant *Escherichia coli* to ampicillin in terms of survival rates of *Escherichia coli* K12BW25113 and ampicillin-resistant bacteria to penicillins, respectively; and FIG. 6C, survival rates of *Escherichia coli* K12BW25113 to tetracycline, erythromycin, clindamycin and rifampicin.

Figure 7:
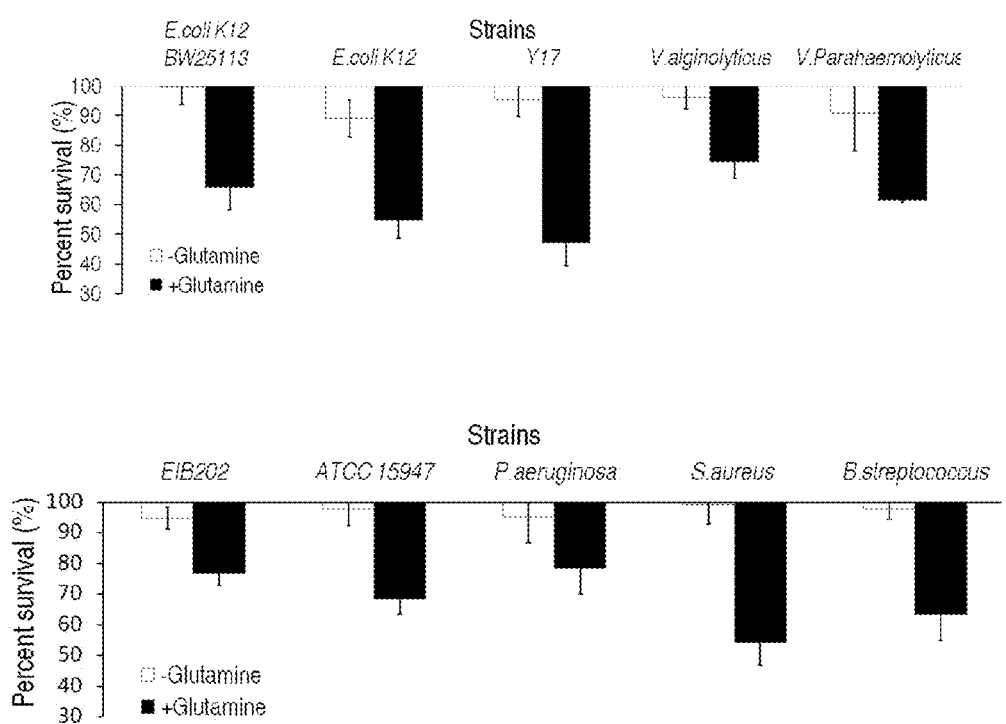

FIG. 7 shows the effect of glutamine on the susceptibility of several species of bacteria to ampicillin.

Figure 8A:
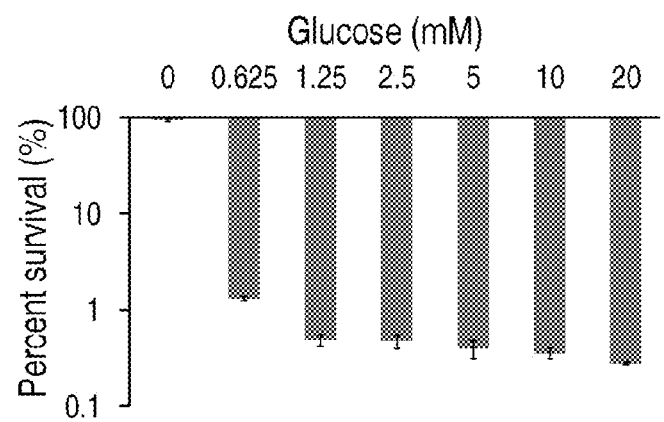
Figure 8B:
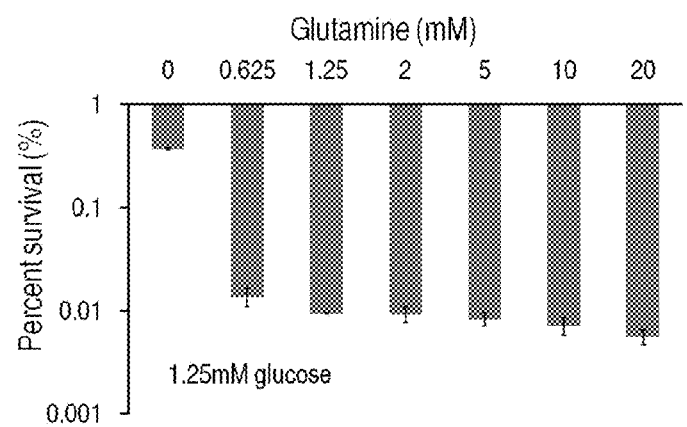
Figure 8C:
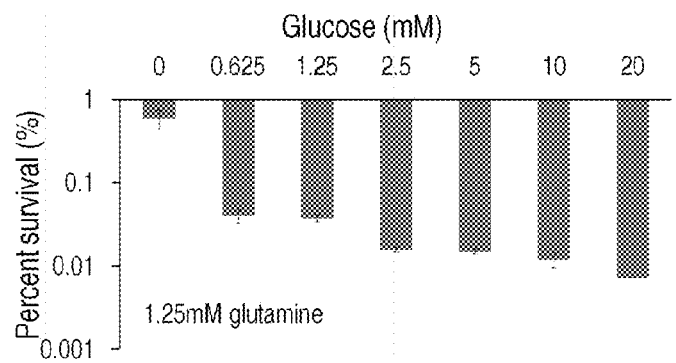

FIG. 8A shows the effect of glucose on the susceptibility of ampicillin-resistant *Escherichia coli* to ampicillin; FIG. 8B shows the effect of glucose on the susceptibility of ampicillin-resistant *Escherichia coli* to ampicillin, and FIG. 8C shows the effect of a combination of glutamine and glucose on the susceptibility of ampicillin-resistant *Escherichia coli* to ampicillin.

Figure 9A:
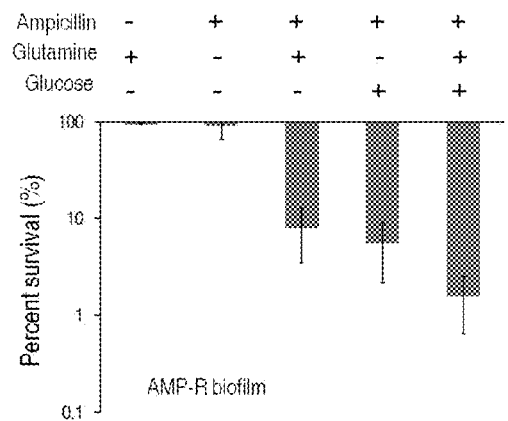
Figure 9B:
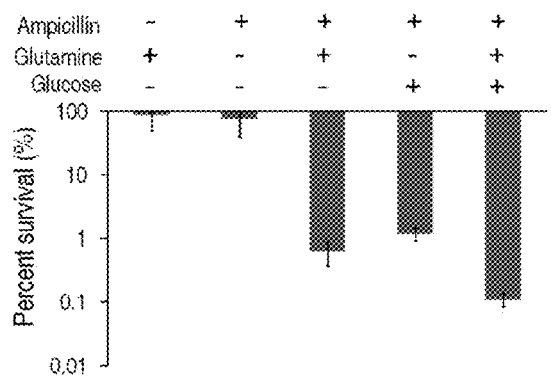
Figure 9C:
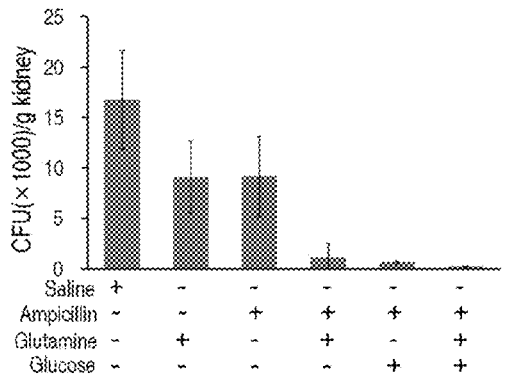

FIG. 9A shows the therapeutic effect of glutamine and glucose combined with ampicillin to ampicillin-resistant bacteria on biofilms; FIGS. 9B and 9C show survival rates of antibiotic-resistant bacteria in the urinary tract and kidney, respectively, of mice.

EMBODIMENTS

The following embodiments is a description of the present invention, for further clear illustration of the present invention but not restriction.

Embodiment 1

Screening of Antibiotic-Resistant *Escherichia coli* K12 BW25113

*Escherichia coli* is a bacterium that is most commonly found in the gut of human and animal. It mainly parasitizes in the intestines, and accounts for about 1% of the intestine bacteria. Minimum inhibitory concentration (MIC) of *Escherichia coli* K12 BW25113 for ten kinds of antibiotics was detected with double dilution method. *Escherichia coli* K12 BW25113 of $10^5$ colony forming unit/ml was cultured respectively in Luria-Bertani (LB) liquid medium separately with each of ten antibiotics at the concentration of ½ MIC at 37° C., and was serially passaged 10 times, so that the MIC of single colony was determined. It was found that the MIC of selected 10 species of bacteria for 10 kinds of antibiotics were 64 times of MIC of respective initial bacteria(shown in Table 1), that was, the 10 antibiotic-resistant *Escherichia coli* were obtained: gentamicin-resistant (GEN-R), ampicillin-resistant (AMP-R), balofloxacin-resistant (BLFX-R), kanamycin-resistant (KAN-R), nalidixic acid-resistant (NA-R), ceftazidime-resistant (CAZ-R), erythromycin-resistant (ER-R), chloramphenicol-resistant (CAP-R), streptomycin-resistant (SM-R) and tetracycline-resistant (TET-R).

TABLE 1

MICs of 10 species *Escherichia coli* before and after passaged in medium with each of 10 kinds of antibiotics

| (μg/mL) | GEN | AMP | BLFX | KAN | NA | CAZ | ER | CAP | SM | TET |
|---|---|---|---|---|---|---|---|---|---|---|
| $MIC_0$ | 1.25 | 6.25 | 0.25 | 6.25 | 5 | 0.125 | 50 | 6.8 | 6.25 | 3.125 |
| $MIC_{10}$ | 80 | 400 | 16 | 400 | 320 | 8 | 3200 | 435.2 | 400 | 200 |
| $MIC_{10}/MIC_0$ | 64 | 64 | 64 | 64 | 64 | 64 | 64 | 64 | 64 | 64 |

GEN: gentamicin,
AMP: ampicillin,
BLFX: balofloxacin,
KAN: kanamycin,
NA: nalidixic acid,
CAZ: ceftazidime,
ER: erythromycin,
CAP: chloramphenicol,
SM: streptomycin,
TET: tetracycline Embodiment 2

Glutamine is a Crucial Biomarker in Ampicillin-Resistant *Escherichia coli*.

1. Preparation the Samples of Ampicillin-Resistant *Escherichia coli* for GC/MS Analysis 1) Preparation of bacterial samples. single colony of *Escherichia coli* K12 BW25113 or ampicillin-resistant *Escherichia coli* (Specific methods for culturing antibiotic resistant bacteria were detailed in Embodiment 1) were cultured in 5 mL LB medium in a shaker at 200 rpm for 16 h at 37° C. The cultures were diluted into 1:100 (v/v) in 100 mL LB medium and incubated to reach OD600 of 1.0 at 37° C.

2) Preparation of GC/MS samples. Bacterial cultures with OD600 of 1.0 were harvested and 5 mL freezing methanol was immediately added into 10 mL bacterial culture to terminate the cellular metabolic processes. After centrifugation at 8000 rpm at 4° C. for 3 min, bacterial pellets were collected and kept in 2 mL cool methanol (Sigma).

3) Extraction of metabolites. Cellular metabolites were extracted with 2 mL cold methanol (Sigma) containing 10 μL of 0.1 mg/mL ribitol (Sigma) as an analytical internal standard. Cells were lysed with sonication at a 60% power setting in an ice bath with 6-s rest and 6-s pulse at a time and repeated five times. Then, the culture was centrifuged at 12,000 g for 5 min at 4° C. The supernatant was transferred into a 1.5 mL centrifuge tube, and then dried in a rotary vacuum centrifuge device (LABCONCO, USA).

4) Derivatization and GC-MS analysis. About 80 μL of 20 mg/mL methoxyamine hydrochloride/pyridine (Sigma-Aldrich) was added into dried samples and reactive at 37° C. for 1.5 h. Subsequently, acidic protons were derivatized with 80 μL N-methyl-N-trimethylsilyltrifluoroacetamide (MSTFA, Sigma-Aldrich) at 37° C. for 0.5 h. The derivatized sample of 1 μL was transferred to micro-vials for further analysis by GC-MS (Trace DSQ II, Thermo Scientific).

GC-MS separation condition. The initial temperature of the GC oven was maintained at 70° C. for 5 min followed by an increase to 270° C. at a rate of 5° C. $\min^{-1}$, then held for 5 min. Injection volume: 1 μL; injection mode: splitless, injector temperature: 270° C.; interface temperature: 270° C.; ion source temperature: 230° C.; quadrupole temperature: 150° C.; Electron impact (EI) ionization was applied at 70 eV. High purity helium was used as carrier gas with a constant flow rate of 1.0 mL $\min^{-1}$. The mass spectra were in full-scan mode a range of 50-600 m/z.

5) Metabolites identification and data processing. Metabolites from the GC-MS spectra were identified by searching in National Institute of Standards and Technology (NIST) library using the NIST MS search 2.0 (NIST Mass Spectral Database, Thermo Scientific). The identification of metabolites was confirmed by comparing their characteristic mass spectra with the same compounds in the standards. The analysis of metabolites in ELMS mass spectra was based to NIST AMDIS (Automated Mass Spectral Deconvolution and Identification System). The resulting data matrixes were normalized by the concentrations of internal standards and the total amount of metabolites.

2. ICA Pattern Recognition.

Figures 1A, 1B:
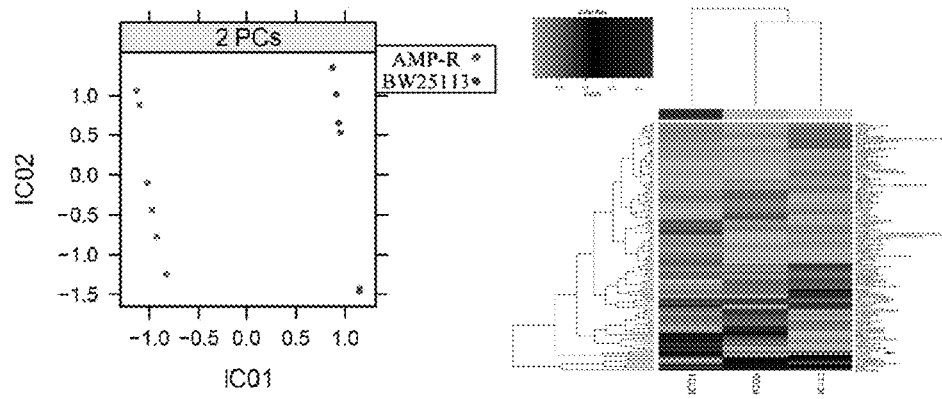
FIG. 1A shows data clustering analysis.
FIG. 1B shows metabolite contents analysis.
Figure 1C:
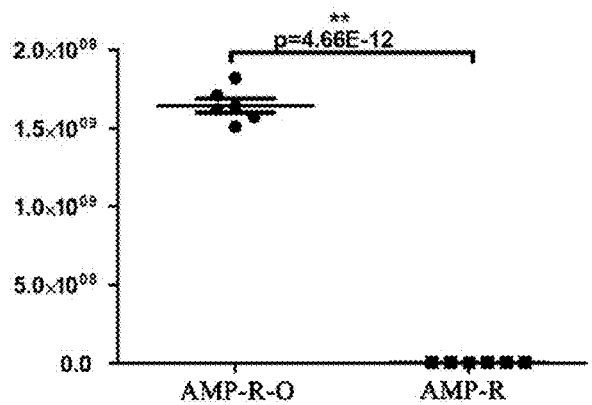
FIG. 1C shows GC-MS for ampicillin-resistant *Escherichia coli* (AMP-R).

Independent component analysis (ICA) was performed on online web (http://metagenealyse.mpimp-golm.mpg.de/). The control bacteria and ampicillin-resistant bacteria (AMP-R) were successfully separated by IC01 component in three independent components (FIG. 1A). Glutamine was considered as significant metabolite in IC01 component and had significant effect on the metabolic profiles (FIG. 1B) in cluster analysis. The amounts of glutamine in control bacteria and ampicillin-resistant bacteria (AMP-R) were further compared. The scatter diagram was plotted with their peak value (FIG. 1C) and found that the amount of glutamine was changed significantly (p<0.01). The result indicates that glutamine is acted as a biomarker in ampicillin-resistant *Escherichia coli*.

Embodiment 3

Decreased Glutamine is Common in Various Species of Antibiotic Resistant *Escherichia coli*

1. Preparation the Samples of Antibiotic Resistant *Escherichia coli* for GC/MS Analysis The control *Escherichia coli* K12 BW25113 and ten antibiotic resistant *Escherichia coli*: GEN-R, AMP-R, BLFX-R, KAN-R, NA-R, CAZ-R, ER-R, CAP-R, SM-R and TET-R were cultured. The methods of sample preparation were described in Embodiment 2.1.

2. Decreased Glutamine was Common in all Species of Antibiotic Resistant *Escherichia coli*.

Figure 2:
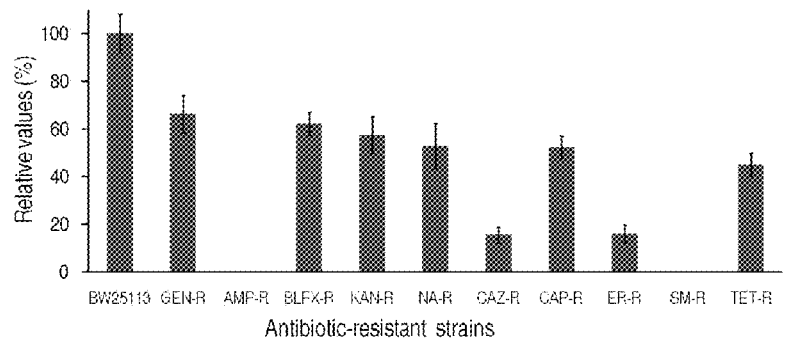
FIG. 2 shows glutamine content analysis in 10 antibiotic resistant bacteria by GC-MS.

The metabolites in the samples of ten species of antibiotic resistant *Escherichia coli* were analyzed by GC-MS. Peaks of glutamine and internal standard ribitol were obtained according to the retention time in total ion chromatograms. The amounts of metabolites were expressed with the ratio of relative peak area (metabolite peak area to internal standard peak area). Glutamine levels in these bacteria were in comparison with the control *Escherichia coli* K12 BW25113 (FIG. 2). The relative amount of glutamine in ten antibiotic resistant *Escherichia coli* (GEN-R, AMP-R, BLFX-R, KAN-R, NA-R, CAZ-R, ER-R, CAP-R, SM-R and TET-R) were 66.23%, 0.62.22%, 59.45%, 57.58%, 13.24%, 57.45%, 15.56%, 0% and 52.24%, respectively, when the amount of glutamine in control bacteria was considered as 100%. These results indicated that decreased glutamine was common in these antibiotic resistant bacteria.

Embodiment 4

Figure 3:
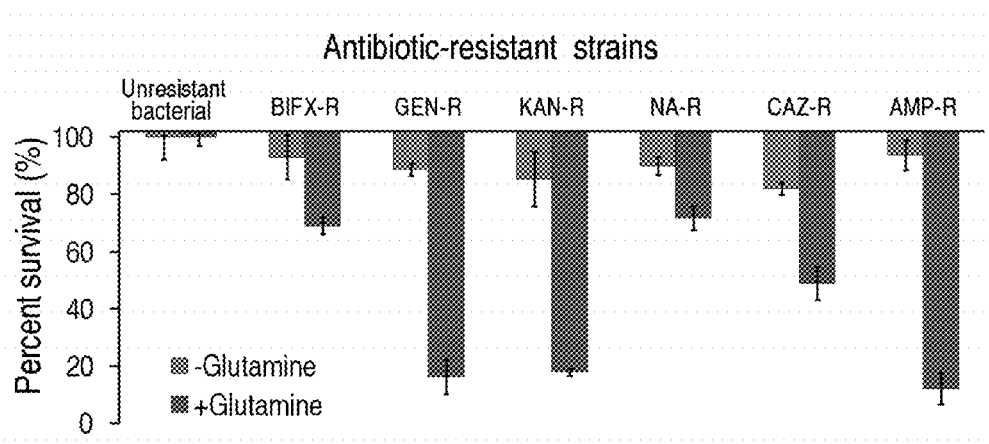
FIG. 3 shows the effect of glutamine on the susceptibility of antibiotic-resistant bacteria to respective antibiotics.

Glutamine can Improve the Sensitivity of *Escherichia coli* and its Antibiotic Resistant Bacteria to Antibiotic 1. Addition of Glutamine Improved the Sensitivity of Different Species of Antibiotic Resistant *Escherichia coli* to Respective Antibiotic Single clones of 6 species of antibiotic resistant *Escherichia coli* (GEN-R, AMP-R, BLFX-R, KAN-R, NA-R and CAZ-R) were cultured in 100 mL LB medium at 200 rpm at 37° C. for 16 h. Bacterium cultures of 20 mL were collected and centrifuged at 8,000 rpm for 5 minutes. The bacterial pellets were washed with equal volume of 0.85% saline solution, suspended in M9 medium containing 10 mM sodium acetate and then adjusted to OD600 of 0.5. Aliquots of 5 mL bacterial suspension were transferred to test tubes and added with 20 mM glutamine and respective antibiotics (8 μg/mL balofloxacin, 50 μg/mL gentamicin, 160 μg/mL nalidixic acid, 160 μg/mL ceftazidime, 160 μg/mL kanamycin or 160 μg/mL ampicillin). These mixtures were cultured in a shaker at 200 rpm at 37° C. for 4 h. Then 100 μL of bacterial suspension was used for bacterial plate counting. Results showed that addition of glutamine improved the sensitivity of 6 species of antibiotic resistant bacteria to respective antibiotic, and about 200 folds elevated sensitivity was detected in ampicillin-resistant bacteria to ampicillin (FIG. 3). Therefore, the sensitivity of ampicillin-resistant bacteria to ampicillin needed further studied.

2. Glutamine Promoted the Sensitivity of Ampicillin-Resistant Bacteria (AMP-R) to Ampicillin.

Further investigations including effects of glutamine concentration, ampicillin concentration and exposure time on the sensitivity of ampicillin-resistant bacteria to ampicillin were conducted.

2.1 Glutamine Increases the Sensitivity of Antibiotic Resistant Bacteria with Antibiotic Concentration Effect.

To investigate the effect of antibiotic dose on the sensitivity of bacteria to antibiotics by glutamine, 20 mM glutamine and 20, 40, 80, 160, 240, 320 and 400 μg/mL ampicillin were used to treat ampicillin-resistant *Escherichia coli* for 4 hours, and then bacterial plate counting was conducted. The survival rates of bacteria with and without glutamine were compared at the same antibiotic concentration. Results showed that the killing efficiency of antibiotic resistant bacteria elevated with the increase of ampicillin concentration after the addition of glutamine, which increased to 200 folds when spiked with 400 μg/mL ampicillin. Specifically, the killing efficiency increased to 1.12 (survival rate from 99.81% to 89.09%), 1.57 (survival rate from 97.27% to 61.82%), 1.95 (survival rate from 95.55% to 49.09%), 7.66 (survival rate from 93.72% to 12.24%), 24.29 (survival rate from 86.72% to 3.57%), 137.78 (survival rate from 83.51% to 0.6%) and 171.34 (survival rate from 67.15% to 0.39%) folds with 20-400 μg/mL ampicillin, respectively, when compared with the treatment without glutamine (FIG. 4A).

2.2 Glutamine Increases the Sensitivity of Antibiotic Resistant Bacteria with Time Effect.

To investigate the effect of exposure time on the killing efficiency, the viable counts of bacteria were counted during 1-8 hours after spiked with 20 mM glutamine and 160 µg/mL ampicillin. Results showed that when added ampicillin to ampicillin-resistant bacteria without glutamine, the viable counts of bacteria remained unchanged during 1-4 hours, and then decreased from 5 hours to 7 hours (survival rate was 74%), final decreased to 66.19% after 8 hours. However, when added with both ampicillin and glutamine, the viable counts of bacteria decreased from the first hour (survival rate was 60.39%) and in a time-dependent manner. Specifically, the killing efficiency increased 8-22 times after 4 hours or more (relative survival rate decreased from 94.27%-66.18% to 12.86%-2.99%) (FIG. 4B).

2.3 Glutamine Increases the Sensitivity of Antibiotic Resistant Bacteria with Glutamine Concentration Effect.

To investigate the effect of glutamine concentration on killing efficiency and the optimum bactericidal concentrations, different concentrations of glutamine were added to 160 µg/mL ampicillin. The number of live bacteria was counted after 4 hours. The survival rate was calculated according to the formula below: viable counts at different concentration of glutamine/viable counts without glutamine×100%. The survival rate of control group (without glutamine) was 94.33%. It decreased from 2.09% to 0.17% with the glutamine concentration increased. The killing efficiency was increase from 45 times to 550 times (FIG. 4C).

3. Glutamine Improved the Sensitivity of Several Species of Antibiotic Resistant *Escherichia coli* to Ampicillin To investigate whether the sensitivity of different species of antibiotic resistant bacteria to ampicillin was improved with glutamine, the samples of control bacteria and antibiotic resistant bacteria were prepared according to Embodiment 2.1. The viable counts and survival rate of bacteria were calculated after added with 20 mM glutamine and 160 µg/mL ampicillin for 4 hours. Results showed that the sensitivity of all antibiotic resistant bacteria to ampicillin increased significantly including the control bacteria when added with glutamine (FIG. 5). The sensitivity of control bacteria increased 1.75 times (survival rate decreased from 74.22% to 42.3%), and 4-36 times for eight species of antibiotic resistant bacteria.

4. Glutamine Improved the Sensitivity of *Escherichia coli* and Antibiotic Resistant *Escherichia coli* to Penicillin Antibiotics To investigate whether the sensitivity of *Escherichia coli* and antibiotic resistant *Escherichia coli* to penicillin antibiotics was improved with glutamine, the samples of control bacteria and penicillin-resistant bacteria were prepared according to Embodiment 2.1. The viable counts and survival rate of bacteria were calculated after added with 20 mM glutamine and 4 kinds of penicillins (does for control bacteria were: ampicillin 25 µg/mL, penicillin G 200 µg/mL, amoxicillin 20 µg/mL, carbenicillin 100 µg/mL; does for antibiotic resistant bacteria were: ampicillin 320 µg/mL, penicillin G 2560 µg/mL, amoxicillin 512 µg/mL, carbenicillin 320 µg/mL) for 4 hours. Results found that glutamine can improve the sensitivity of control bacteria (FIG. 6A) and antibiotic resistant bacteria (FIG. 6B) to four types of penicillins. The sensitivity of control bacteria increased 38-1000 times and 71-1900 times for 4 antibiotic resistant bacteria when added with glutamine.

5. Glutamine Improved the Sensitivity of *Escherichia coli* to Other Antibiotics To investigate whether the sensitivity of *Escherichia coli* to other antibiotics was improved with glutamine, the samples of control bacteria (*Escherichia coli* K12 BW25113) were prepared according to Embodiment 2.1. The viable counts and survival rate of bacteria were calculated after added with 20 mM glutamine and antibiotics at the concentration of 8 times of MIC for 4 hours. The antibiotics used were tetracycline, erythromycin, clindamycin and rifampicin. Results showed that glutamine can improve the sensitivity of control bacteria to 4 kinds of antibiotics by approximately 1.5 times (FIG. 6C).

In summary, glutamine not only improves the sensitivity of antibiotic resistant *Escherichia coli* to respective antibiotics, but also to ampicillin and 3 other types of penicillins. This approach is also suitable for the treatment of non-resistant bacteria. Therefore, combined utilization of antibiotic and glutamine may be effective to treat with the infection caused by antibiotic resistant or non-resistant bacteria by improving the bacterial sensitivity to antibiotics. Especially, the combination of ampicillin and glutamine is general effective to inhibit the viability of antibiotic resistant bacteria.

Embodiment 5

Glutamine Improved the Sensitivity of Several Species of Bacteria to Ampicillin

Single clones of *Staphylococcus aureus, Edwardsiella tarda* (EIB202, ATCC15947), *Beta streptococcus, Pseudomonas aeruginosa, Escherichia coli* (K12 BW25113, *E. coli* K12, Y17), *Vibrio alginolyticus* and *Vibrio parahaemolyticus* were isolated and inoculated in 100 mL LB medium and cultured at 200 rpm at 37° C. (*Staphylococcus aureus, B. streptococcus, Pseudomonas aeruginosa, Escherichia coli*) or 30° C. (the others) for 16 hours.

Bacterium suspension of 20 mL were collected and centrifuged at 8,000 rpm for 5 min. The resulting bacterial pellets were washed with equal volume of 0.85% saline solution, suspended in M9 medium containing 10 mM sodium acetate and then adjusted to OD600 of 0.5. Aliquots of 5 mL bacterial suspension were transferred to test tubes and added with 20 mM glutamine and ampicillin (double minimum inhibitory concentration for each bacterial strain). These mixtures were cultured in a shaker at 200 rpm at 37° C. for 4 hours. Then 100 µL of bacterial suspension was used for bacterial plate counting and the survival rate was calculated. The results were shown in FIG. 7. From these results it can be seen that the sensitivity of these bacteria to ampicillin was improved generally after added with glutamine.

Embodiment 6

Glutamine and glucose synergy improved the sensitivity of antibiotic resistant bacteria to antibiotics It was reported that glucose can improve the sensitivity of gram-positive bacteria (*Escherichia coli*) and gram-negative bacteria (*Staphylococcus aureus*) to aminoglycosides, which was specific to this class of aminoglycoside antibiotics. Hence, effect of the combination of glutamine and glucose on the sensitivity of ampicillin-resistant *Escherichia coli* to ampicillin was studied.

1. Preparation of Ampicillin-Resistant *Escherichia coli*

Single clone of ampicillin-resistant *Escherichia coli* was selected and inoculated in 100 mL LB medium and cultured at 200 rpm at 37° C. for 16 hours. Bacterial suspension of 20 mL was collected and centrifuged at 8,000 rpm for 5 min. The resulting bacterial pellets were washed with equal volume of 0.85% saline solution, suspended in M9 medium containing 10 mM sodium acetate and then adjusted to OD6 of 0.5. Aliquots of 5 mL bacterial cells were transferred to test tubes for further application.

2. Glucose Improved the Sensitivity of Ampicillin-Resistant *Escherichia coli* to Ampicillin The sample was added with 160 μg/mL ampicillin and 0-20 Mm glucose, then cultured in a shaker at 200 rpm at 37° C. for 4 hours. The cell number was counted and survival rate was calculated. Results showed that the survival rate in control group (without glucose) was 94.33%, which decreased from 1.31% to 0.27% after added with increasing glucose, the killing efficiency increased from 71 times to 338 times (FIG. 8A). The results indicated that glucose can improve the sensitivity of ampicillin-resistant *Escherichia coli* to ampicillin.

3. Glutamine and Glucose Synergy Improved the Sensitivity of Ampicillin-Resistant Bacteria to Ampicillin To investigate the synergistic effect of glutamine and glucose on the sensitivity of ampicillin-resistant bacteria to ampicillin, two groups of experiments were conducted. One group was added with 1.25 mM glucose and 0-20 mM glutamine; the other group was added with 1.25 mM glutamine and 0-20 mM glucose; both groups were added with 160 μg/mL ampicillin. The samples were cultured in a shaker at 200 rpm at 37° C. for 4 hours. Then the cell number was counted and survival rate was calculated. Results showed that the sensitivity of antibiotic-resistant bacteria increased significantly when the samples were added with one substance and another substance with the minimum concentration. For example, bacterial sensitivity increased by 27 and 65 times in 1.25 mM glucose plus 0.625 and 20 mM glutamine, respectively. Similarly, the sensitivity elevated by 14 and 81 folds in 1.25 mM glutamine plus 0.625 and 20 mM glucose (FIGS. 8B and C).

Embodiment 7

Glutamine significantly improved the elimination of ampicillin-resistant *Escherichia coli* biofilm in vitro and in vivo.

Single clone of ampicillin-resistant *Escherichia coli* was selected and incubated in LB medium overnight, then transferred into 2 mL fresh LB medium according to the proportion of 1:200 dilutions and transferred to 6 mm ultraviolet sterilized PE-50 catheters. The catheters were inoculated in 1 mL LB at 37 for 24 h. The culture medium was changed every 24 hours for 3 days. The biofilm of ampicillin-resistant bacteria in PE50 catheters were washed with 1 mL sterile phosphate-buffered saline five times to remove loosely adherent cells, and then transferred to 1.5 mL EP tubes.

The test was divided into six groups: saline solution control, 20 mM glutamine, 160 μg/mL ampicillin, 160 μg/mL ampicillin plus 20 mM glutamine, 160 μg/mL ampicillin plus 20 mM glucose, 160 μg/mL ampicillin plus 20 mM glutamine and 20 mM glucose. The catheters were cultured in a shaker at 200 rpm at 37 for 6 hours. The bacterial biofilm was removed from catheters with sonication for 10 minutes. Serial dilutions and spot-plating were performed to determine the cell number. The bacterial survival rate was calculated as: viable counts in treatment group/viable counts in control group×100%. Results showed that the survival rates of 5 treatment group were 96.03%, 92.84%, 8.08%, 5.62% and 1.58%, respectively (FIG. 9A). These results indicated that: 1) Glutamine or ampicillin alone did not eliminate the antibiotic-resistant bacterium biofilm, but synergy of glutamine and ampicillin increased the elimination of antibiotic-resistant *Escherichia coli* effectively by 11 folds; 2) Synergy of glucose and ampicillin increased the elimination of antibiotic-resistant *Escherichia coli* by 16.5 folds; 3) Combination of glutamine and glucose plus ampicillin increased by 5 and 3 folds in comparison with the combination of ampicillin with glutamine or glucose, respectively.

In vivo experiments in mice, female mice (5 weeks, weighing 18-20 g) received surgical implantation in the urinary tract of PE50 catheter tubes. The mice were randomly divided into six groups in 48 h after the surgery, five each group. The six groups included treatment with saline (group 1), 100 mg $kg^{-1}$ glutamine (group 2), 320 mg $kg^{-1}$ ampicillin (group 3), 100 mg $kg^{-1}$ glutamine plus 320 mg $kg^{-1}$ ampicillin (group 4), 100 mg $kg^{-1}$ glucose plus 320 mg $kg^{-1}$ ampicillin (group 5), and 100 mg $kg^{-1}$ glutamine and 100 mg $kg^{-1}$ glucose plus 320 mg $kg^{-1}$ ampicillin (group 6) by tail intravenous injection for 3 days, twice-daily. Catheter tubes were extracted in 24 hours after the last treatment. To dislodge biofilm cells, catheters were suspended in saline solution with ultrasonic. Serial dilutions and spot-plating were performed to determine the bacterial survival rate in biofilm. The survival rate was calculated as: viable counts in treatment group/viable counts in control group×100%. Results showed that the survival rates of 5 treatment groups were 88.24%, 76.81%, 0.63%, 1.19% and 0.11%, respectively, in comparison with that of saline solution control (FIG. 9B). These data indicated that: 1) Cell viability reduced significantly in the group with glutamine and ampicillin, reduced by 140 and 120 times compared with the groups with glutamine or ampicillin alone, respectively; 2) Killing efficiency increased by 65 times when added with antibiotics and glucose; 3) The best effect was detected in the group with glutamine and glucose plus ampicillin, which increased by 5 and 10 folds in comparison with those of glutamine or glucose alone plus ampicillin.

Meanwhile, kidneys of mice were homogeneous with appropriate amount of saline. Bacterial content in kidneys was determined by plate counting method. Results showed that the bacterial contents were 16750, 9113, 9129, 1107, 660 and 193 cell/g in the 1-6 groups, respectively (FIG. 9C). These data indicate that: 1) Bacterial content in the group 4 with ampicillin and glutamine reduced by 15, 8 and 8 folds in comparison with saline (group 1), glutamine (group 2) and ampicillin (group 3) controls; 2) Bacterial contents reduced by 13 folds in group 5 compared with group 1; 3) Combination of glutamine and glucose plus ampicillin increased the elimination of antibiotic-resistant bacteria by 5 and 3 folds in comparison with glutamine or glucose plus ampicillin, respectively.

Based on the above animal testing, it is indicated that glutamine can improve the sensitivity of ampicillin-resistant bacteria to penicillins. Moreover, glutamine and glucose have synergistic effect, when used together the effect was better.

What is claimed is:

1. A method of treating an individual having a microbial infection, the method comprising:
   administering an antibiotic, a potentiating amount of glutamine, and a potentiating amount of glucose to the individual that has been determined to have the microbial infection, wherein:
   the microbial infection comprises a microbe selected from the group consisting of *Escherichia coli, Staphylococcus aureus, Edwardsiella tarda, Beta hemolytic streptococcus, Pseudomonas aeruginosa*, and *Vibrio spp.*;
   the antibiotic is selected from the group consisting of ampicillin, amoxicillin, penicillin G, carbenicillin, ceftazidime, balofloxacin, nalidixic acid, gentamicin, kanamycin, erythromycin, tetracycline, rifampicin and clindamycin;

the potentiating amount of the glutamine is sufficient to augment the activity of the antibiotic synergistically for treating the microbial infection;

the potentiating amount of the glucose is sufficient to augment the activity of the antibiotic and the glutamine synergistically for treating the microbial infection;

the glutamine and the glucose are administered at a ratio of the glutamine to the glucose of 1:0.031-32 (mole to mole); and the glutamine and the antibiotic are administered at a ratio of the glutamine to the antibiotic of 1:0.0015-300 by weight.

2. A pharmaceutical composition for treating an individual having a microbial infection, the composition comprising an antibiotic, a potentiating amount of glutamine, a potentiating amount of glucose, and a pharmaceutically acceptable carrier, wherein:

the microbial infection comprises a microbe selected from the group consisting of *Escherichia coli, Staphylococcus aureus, Edwardsiella tarda, Beta hemolytic streptococcus, Pseudomonas aeruginosa*, and *Vibrio spp.;* the antibiotic is selected from the group consisting of ampicillin, amoxicillin, penicillin G, carbenicillin, ceftazidime, balofloxacin, nalidixic acid, gentamicin, kanamycin, erythromycin, tetracycline, rifampicin and clindamycin;

the potentiating amount of the glutamine is sufficient to augment the activity of the antibiotic synergistically for treating the microbial infection;

the potentiating amount of the glucose is sufficient to augment the activity of the antibiotic and the glutamine synergistically for treating the microbial infection;

the glutamine and the glucose are present at a ratio of the glutamine to the glucose of 1:0.031-32 (mole to mole); and the glutamine and the antibiotic are administered at a ratio of the glutamine to the antibiotic of 1:0.0015-300 by weight.

3. A method of treating an individual having a microbial infection by promoting a killing efficiency of an antimicrobial agent based on use of glutamine, glucose, and the antimicrobial agent, the method comprising:

administering the antimicrobial agent, a potentiating amount of the glutamine, and a potentiating amount of glucose to the individual that has been determined to have the microbial infection, wherein:

the microbial infection comprises a microbe selected from the group consisting of *Escherichia coli, Staphylococcus aureus, Edwardsiella tarda, Beta hemolytic streptococcus, Pseudomonas aeruginosa*, and *Vibrio spp.;* the antimicrobial agent is selected from the group consisting of ampicillin, amoxicillin, penicillin G, carbenicillin, ceftazidime, balofloxacin, nalidixic acid, gentamicin, kanamycin, erythromycin, tetracycline, rifampicin and clindamycin;

the potentiating amount of the glutamine is sufficient to augment the activity of the antimicrobial agent synergistically for treating the microbial infection;

the potentiating amount of the glucose is sufficient to augment the activity of the antibiotic and the glutamine synergistically for treating the microbial infection;

the glutamine and the glucose are administered at a ratio of the glutamine to the glucose of 1:0.031-32 (mole to mole); and the glutamine and the antimicrobial agent are administered at a ratio of the glutamine to the antimicrobial agent of 1:0.0015-300 by weight.

4. The method according to claim 3, wherein the microbe comprises antibiotic-resistant bacteria.

* * * * *